(12) United States Patent
Schick et al.

(10) Patent No.: US 7,193,219 B2
(45) Date of Patent: *Mar. 20, 2007

(54) INTRAORAL IMAGE SENSOR (75) Inventors: David B. Schick, Flushing, NY (US);
Stan Mandelkern, Teaneck, NJ (US);
Valeriy Armencha, Brewster, NY (US)

(73) Assignee: Schick Technologies, Inc., Long Island City, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 11/414,180

(22) Filed: May 1, 2006

(65) Prior Publication Data

US 2006/0193436 A1    Aug. 31, 2006

Related U.S. Application Data

(62) Division of application No. 10/315,007, filed on Dec. 10, 2002, now Pat. No. 7,072,443.

(60) Provisional application No. 60/415,716, filed on Oct. 3, 2002.

(51) Int. Cl.
*G01T 1/20* (2006.01)
(52) U.S. Cl. .............................. 250/370.11; 250/370.09; 378/98.8
(58) Field of Classification Search .................. 378/98, 378/98.8, 168, 191; 250/370.11, 370.09
See application file for complete search history.

(56) References Cited

U.S. PATENT DOCUMENTS

| | | | |
|---|---|---|---|
| 4,082,953 A | 4/1978 | Krause et al. ............... 250/413 |
| 4,160,997 A | 7/1979 | Schwartz ...................... 358/93 |
| 4,494,950 A | 1/1985 | Fischell ........................ 604/66 |
| 4,575,805 A | 3/1986 | Moermann et al. ......... 364/474 |
| 4,629,424 A | 12/1986 | Lauks et al. .................... 433/6 |
| 4,633,304 A | 12/1986 | Nagasaki ...................... 358/98 |
| 4,658,669 A | 4/1987 | Nishikawa .................... 74/531 |
| 4,835,410 A | 5/1989 | Bhagwat et al. .............. 307/64 |
| 4,858,001 A | 8/1989 | Milbank et al. .............. 358/98 |
| 4,981,141 A | 1/1991 | Segalowitz .................. 128/696 |
| 4,987,897 A | 1/1991 | Funke ......................... 128/419 |
| 5,113,859 A | 5/1992 | Funke ......................... 128/419 |
| 5,115,307 A | 5/1992 | Cooper et al. ................ 358/98 |
| 5,212,476 A | 5/1993 | Maloney ................ 340/825.19 |
| 5,231,653 A | 7/1993 | Pfeiler et al. ................. 378/91 |
| 5,233,662 A | 8/1993 | Christensen ................. 381/70 |
| 5,257,184 A | 10/1993 | Mushabac .............. 364/413.28 |
| 5,264,935 A | 11/1993 | Nakajima .................... 358/181 |
| 5,373,852 A | 12/1994 | Harrison et al. ............ 128/733 |
| 5,434,418 A | 7/1995 | Schick ................... 250/370.11 |

(Continued)

*Primary Examiner*—Edward J. Glick
*Assistant Examiner*—Jurie Yun
(74) *Attorney, Agent, or Firm*—Fitzpatrick, Cella, Harper & Scinto (57) ABSTRACT

An intraoral sensor includes a radiation sensitive sensor array, an event detection circuit, and a transmitter. The radiation sensitive sensor array includes a scintillator which converts x-rays into visible light radiation, and a plurality of pixels sensitive to visible light radiation to capture an image upon the presence of incident radiation. The event detection circuit includes a current sensing device and is configured to generate a triggering signal indicating the presence of radiation incident on the sensor array based upon the amount of electrical current drawn by the sensor array. The transmitter is adapted to transmit via a wireless link signals representing an image captured by the sensor array.

7 Claims, 4 Drawing Sheets

U.S. PATENT DOCUMENTS

| | | | |
|---|---|---|---|
| 5,454,022 A | 9/1995 | Lee et al. | 378/98.8 |
| 5,471,515 A | 11/1995 | Fossum et al. | 377/60 |
| 5,471,518 A | 11/1995 | Barber et al. | 379/58 |
| 5,510,623 A | 4/1996 | Sayag et al. | 250/370.11 |
| 5,513,252 A | 4/1996 | Blaschka et al. | 378/98.8 |
| 5,514,873 A | 5/1996 | Schulze-Ganzlin et al. | 250/394 |
| 5,527,261 A | 6/1996 | Monroe et al. | 600/109 |
| 5,551,953 A | 9/1996 | Lattin et al. | 604/20 |
| 5,712,482 A | 1/1998 | Gaiser et al. | 250/363.08 |
| 5,745,165 A | 4/1998 | Atsuta et al. | 348/65 |
| 5,873,814 A | 2/1999 | Adair | 600/109 |
| 5,877,501 A | 3/1999 | Ivan et al. | 250/370.09 |
| 5,879,289 A | 3/1999 | Yarush et al. | 600/179 |
| 5,880,826 A | 3/1999 | Jung et al. | 356/73 |
| 5,908,294 A | 6/1999 | Schick et al. | 433/29 |
| 6,069,935 A | 5/2000 | Schick et al. | 378/98.8 |
| 6,132,211 A | 10/2000 | Peithman | 433/29 |
| 6,134,298 A | 10/2000 | Schick et al. | 378/98.8 |
| 6,149,300 A | 11/2000 | Greenway et al. | 378/191 |
| 6,186,944 B1 | 2/2001 | Tsai | 600/200 |
| 6,295,337 B1 | 9/2001 | Thevenin et al. | 378/117 |
| 6,320,934 B1 | 11/2001 | Carroll et al. | 378/98.8 |
| 6,339,633 B1 | 1/2002 | Hull et al. | 378/91 |
| 6,402,707 B1 | 6/2002 | Ernst | 600/590 |
| 6,404,854 B1 | 6/2002 | Carroll et al. | 378/98.8 |
| 6,761,561 B2 | 7/2004 | Mandelkern et al. | 433/29 |
| 6,797,960 B1 | 9/2004 | Spartiotis et al. | 250/370.09 |
| 6,924,486 B2 | 8/2005 | Schick et al. | 250/370.08 |
| 6,972,411 B2 | 12/2005 | Schick et al. | 250/370.11 |
| 2001/0052930 A1 | 12/2001 | Adair et al. | 348/65 |
| 2001/0055368 A1 | 12/2001 | Carroll | 378/189 |
| 2002/0150214 A1 | 10/2002 | Spahn | 378/189 |
| 2003/0185338 A1 | 10/2003 | Dafni et al. | 378/15 |

INTRAORAL IMAGE SENSOR

CROSS-REFERENCE TO RELATED APPLICATION

This application is a divisional of U.S. application Ser. No. 10/315,007, filed Dec. 10, 2002, which issued as U.S. Pat. No. 7,072.443 B2 on Jul. 4, 2006, and which claims the benefit of U.S. provisional application No. 60/415,716, filed Oct. 3, 2002, the entire contents of each of which are incorporated herein by reference.

BACKGROUND OF THE INVENTION

1. Field of the Invention

This invention relates to a filmless dental radiography system, and more particularly to a filmless dental radiography system that includes an intra-oral radiation sensor that can acquire and display an entire full-mouth series of images without needing to be removed from a patient's mouth.

2. Description of the Related Art

Dentists and oral surgeons typically use x radiation to obtain images of their patient's teeth, mouths and gums to aid in diagnosis and treatment. In traditional oral and dental radiography, a cartridge containing photographic film is placed in the patient's mouth, for example behind a patient's tooth, and an x-ray beam is projected through the tooth and onto the film. The film, after being exposed in this manner, is developed in a dark room or a closed processor using special chemicals to obtain a photographic image of the tooth.

More recently, the field of filmless dental radiography has emerged. In filmless dental radiography, an x-ray beam is still projected through the patient's tooth, but no photographic film is used. Instead, an electronic sensor is placed in the patient's mouth behind the tooth to be examined. The electronic sensor may include a charge-coupled device (CCD), a complementary metal-oxide semiconductor (CMOS) active pixel sensor (APS) array or any other filmless radiation sensor. The x-rays pass through the tooth and impinge on the electronic sensor, which converts the x-rays into an electrical signal. The electrical signal is transmitted to a computer, either directly or through a module containing intermediate processing circuitry. The computer then processes the signal to produce an image on an associated output device, such as a monitor or a printer.

Filmless dental radiography offers several advantages over traditional film-based radiography. Most importantly, the electronic sensor is much more sensitive to x-rays than is film, allowing the dosage of x-rays to the patient to be lowered by as much as 90%. Also, the image of the tooth is generated by the computer almost instantaneously, thus eliminating the entire development process, including the use of potentially harmful chemicals. In addition, because the images are generated electronically, they can be stored electronically in a computer database.

Examples of filmless dental radiography systems include those described in U.S. Pat. No. 4,160,997 to Robert Schwartz and U.S. Pat. No. 5,434,418 to David Schick.

Filmless dental radiography systems typically utilize a cable to connect the intraoral sensor to the computer or processing module. Such a cable, however, can be uncomfortable for and annoying to the patient in whose mouth the intraoral sensor is placed. The cable is also bothersome to the dental practitioner when positioning the sensor in the patient's mouth. It would be advantageous to both patient and practitioner, therefore, if the cable connecting the intraoral sensor to the computer or processing module could be eliminated.

A filmless dental radiography system that attempts to solve the problem of the cable is described in U.S. Pat. No. 5,514,873 to Schulze-Ganzlin et al. In a first embodiment described in Schulze-Ganzlin, a radiation detector is inserted into the mouth of the patient in a manner similar to the manner in which conventional x-ray film is exposed. Images are captured by converting incident x-radiation to electrical signals, which electrical signals in turn are conducted via the control logic to an electromechanical coupling element. After the image is captured, the detector is removed from the patient's mouth and physically coupled to an evaluation unit via the electromechanical coupling element. The signals from the detector are sent to the evaluation unit via the electromechanical coupling element, and the evaluation unit processes the signal into an image. After the signals have been read out of the detector in this fashion, the detector is reset to prepare it for the next exposure. The detector is uncoupled from the evaluation unit and re-inserted into the next position in the patient's mouth.

While this arrangement operates without using a cable to connect the sensor, the radiation detector must be removed from the mouth and inserted into the evaluation unit after each image is captured. Thus, for a standard set of eighteen x-rays, the process of (1) positioning the radiation detector in the patient's mouth; (2) exposing the detector; (3) removing it from the patient's mouth; and (4) inserting it into the evaluation unit must be repeated eighteen times. This approach is plainly cumbersome, and in fact is less desirable than a system that uses a cable, since in a cable system images are obtained instantly without removing the sensor from the patient's mouth, and the sensor can be moved directly from one position in the mouth to the next.

A second embodiment described by Schulze-Ganzlin uses a wireless transceiver in place of the electromechanical coupling element and adds a memory. The memory stores multiple images, so that the radiation detector need not be removed from the mouth and inserted into the evaluation unit between each exposure. Instead, the radiation detector can be moved directly from one position to the next position inside the mouth until all the desired images are captured. The communication from the wireless transceiver to the evaluation unit is either inductive, capacitive or electro-optical. Accordingly, once all the images have been captured, the radiation detector must still be removed from the mouth and placed in close proximity to the evaluation unit so that the stored signals can be read out.

Even with this approach, however, there are a number of disadvantages. First of all, because the radiation detector must be removed from the mouth to be read out, instantaneous images still cannot be obtained. Thus, this approach shares a disadvantage with traditional film-based x-rays: images cannot be viewed until all the images are collected and subsequently transmitted into the console. As a result, there is no way to know when a given image is defective until after the radiation detector is removed from the patient's mouth. Moreover, the detector is necessarily more complex because significant memory must be provided, along with a control system capable of recognizing exactly when a given image is to be captured and stored. This second approach, therefore, is again less desirable than cable-based systems.

Another wireless system is described in U.S. Pat. No. 5,454,022 to Lee et al. In Lee, an intraoral sensor includes a CCD, CCD control and processing circuits, a battery, an analog-to digital converter (ADC) and a transmitter; and a base image system includes a receiver, a display and a power supply connector. In this invention, the sensor must be re-connected to the base station following each exposure. A second limitation is that the sensor must be maintained in the record mode for a previously set predetermined period of time while the image sensor is physically and electrically isolated from the base station. Timing each exam like this would be quite cumbersome for the dentist. It would be more desirable to have an efficient mechanism for automatically triggering image acquisition.

There is a need, therefore, for a filmless dental radiography system that eliminates the cable between the sensor and the computer, and overcomes the obstacles that plague the systems in the prior art.

SUMMARY OF THE INVENTION

One object of the present invention is to provide a wireless filmless dental radiography system.

Another object of the present invention is to provide a wireless filmless dental radiography system in which a reliable image signal is transmitted from within a patient's oral cavity to a receiver located outside of a patient's oral cavity.

Another object of the present invention is to provide a wireless filmless dental radiography system which allows diagnostic quality images from an entire exam to be obtained and viewed instantaneously, and multiple images to be taken without removing the sensor from the patient's mouth.

Yet another object of the present invention is to provide a wireless filmless dental radiography system in which triggering is activated within the pixel array itself.

Yet another object of the present invention is to provide a wireless filmless dental radiography system in which the intraoral sensor can be operated in a manner that efficiently conserves power consumption.

In one embodiment of the present invention, a system for capturing intraoral images comprises an intraoral oral sensor. The sensor includes a radiation sensitive sensor array, a transmitter, and a power source that provides power to the sensor array and the transmitter. The sensor is configured to be inserted into a patient's oral cavity, capture an image upon the presence of incident radiation and transmit from within the oral cavity via a wireless link electrical signals representing the image. The system further includes a base station positioned outside the oral cavity configured to receive the electrical signals transmitted by the sensor via the wireless link. The sensor is capable of capturing and transmitting to the base station electrical signals representing multiple images without requiring that the sensor be removed from the oral cavity.

In another embodiment of the present invention, an intraoral sensor comprises a first subsystem that includes a radiation sensitive sensor array that captures an image upon the presence of incident radiation, a second subsystem that includes a transmitter that transmits via a wireless link signals representing an image captured by the sensor array, a third subsystem that includes a power source that provides power to the first subsystem and the second subsystem, and a fourth subsystem that includes a controller that selectively controls the provision of power by the third subsystem to the first subsystem and the second subsystem.

In yet another embodiment of the present invention, an intraoral sensor comprises a radiation sensitive sensor array that captures an image upon the presence of incident radiation and an event detection circuit including a current sensing device. The event detection circuit is configured to generate a triggering signal indicating the presence of radiation incident on the sensor array, based upon the amount of electrical current drawn by the sensor array. The intraoral sensor further comprises a transmitter adapted to transmit via a wireless link signals representing an image captured by the sensor array.

In still another embodiment of the present inventions, an intraoral sensor comprises a first subsystem that includes a radiation sensitive sensor array that captures an image upon the presence of incident radiation. The intraoral sensor further comprises a second subsystem that includes an analog-to-digital converter that converts analog signals representing an image captured by the sensor array into digital image signals, a logic circuit that conditions the digital image signals into a format suitable for transmission via a wireless link and a transmitter that transmits via the wireless link the conditioned digital image signals. The intraoral sensor further includes a third subsystem that includes a power source that provides power to said first subsystem and said second subsystem and a fourth subsystem that includes a controller that selectively controls the provision of power by the third subsystem to the first subsystem and the second subsystem.

DETAILED DESCRIPTION OF THE PREFERRED EMBODIMENTS

Figure 1:
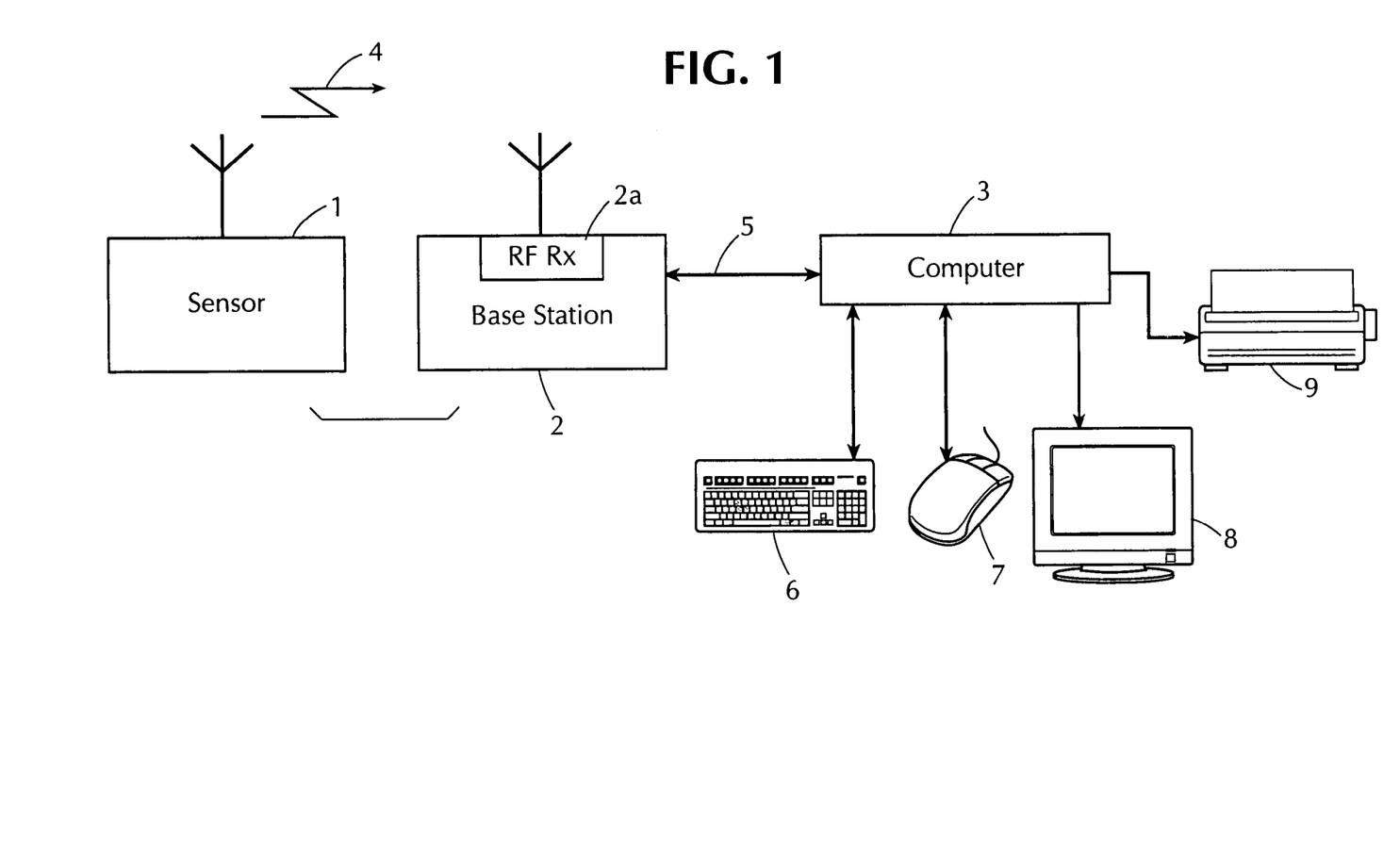
FIG. 1 is a block level illustration of one embodiment of the dental radiography system of the present invention.

An embodiment of a filmless dental radiography system according to the present invention is depicted in FIG. 1. The system includes an intraoral sensor 1, a base station 2 that includes a radio frequency (RF) receiver 2a and data output ports (not shown), and a host computer 3. The sensor 1 is placed in the patient's oral cavity, and communicates with the RF receiver 2a of the base station 2, which is located outside the oral cavity, via wireless RF link 4, as will be discussed in greater detail below. The base station 2 communicates with the host computer 3 over a bi-directional wired link 5.

Preferably, the communication between the base station 2 and host computer 3 is via the widely available and accessible Universal Serial Bus port, as described in U.S. Pat. No. 6,134,298 assigned to the assignee of the present invention and hereby incorporated by reference. Alternatively, the base station 2 may communicate with the host computer 3 via the computer's Peripheral Component Interconnect (PCI) bus, a high-speed Firewire bus, or via the computer's Industry Standard Architecture (ISA) bus. In such a case, a special purpose board normally would be housed in the host computer 3 to facilitate such communication. In any case, the communication between the sensor 1 and host computer 3 should be direct and nearly instantaneous.

The host computer 3 may be any conventional desktop, tower, laptop or notebook computer, equipped with software for processing the data provided to it. The computer 3 is either connected to or has built in one or more input devices, such as a keyboard 6 or a mouse 7, and one or more output devices, such as a monitor 8 or a printer 9. These devices allow the user to control the operation of the system, and to view the dental images that the system creates. The computer might also include or be connected to some type of storage device (not shown), such as a hard drive, for permanent storage of the images in patient files.

Figure 2:
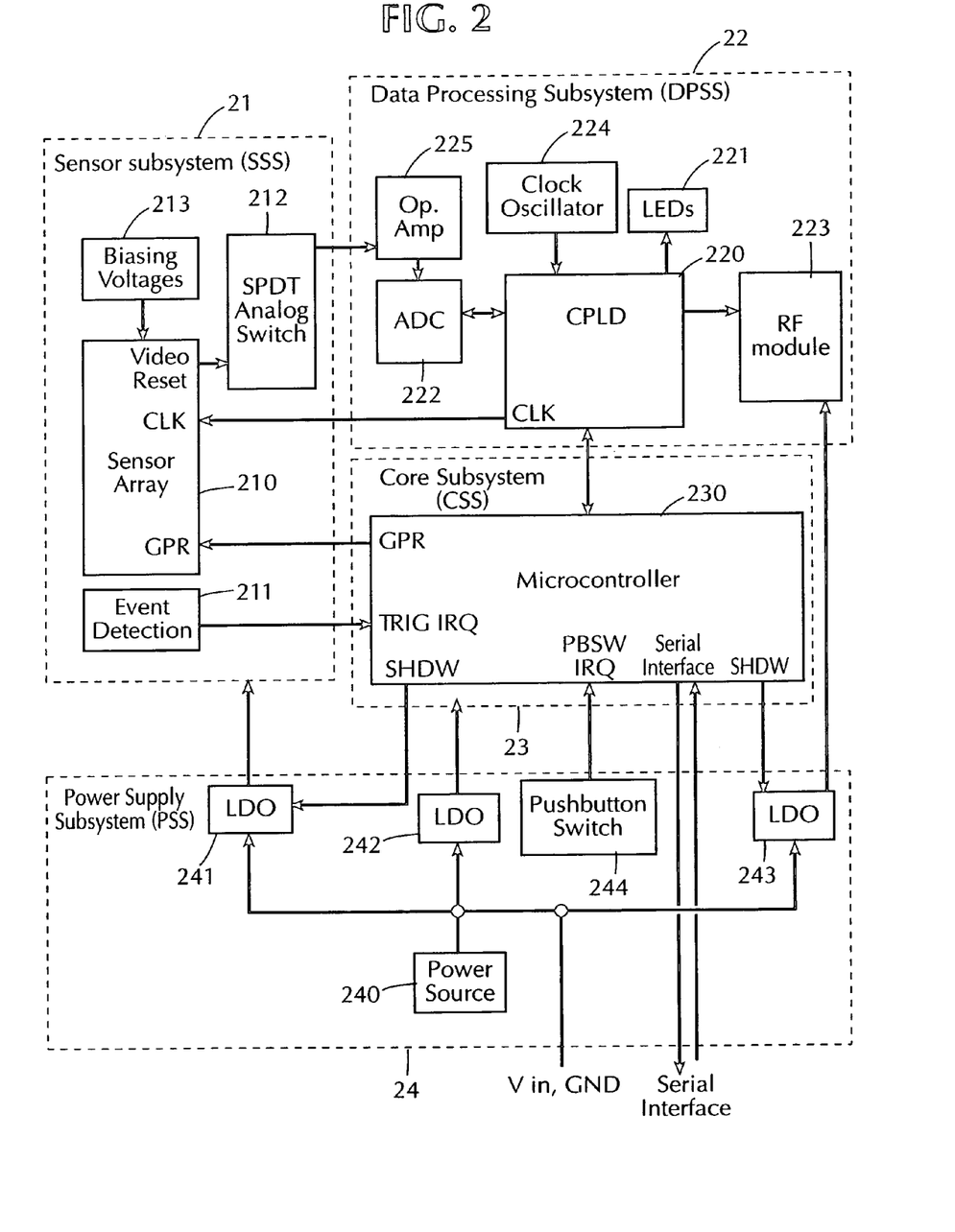
FIG. 2 is a block level illustration of one embodiment of the intraoral sensor of the present invention.

An embodiment of the intraoral sensor 1 is depicted schematically in FIG. 2. The sensor 1 in this embodiment is divided into four subsystems: a Sensor Subsystem (SSS) 21 that includes the actual sensor array 210, an event detection module 211, a single-pole double-throw analog switch 212 and a biasing voltages module 213; a Data Processing Subsystem (DPSS) 22 that includes a complex programmable logic device (CPLD) 220 (which among other things provides clock signals CLK to the sensor array 210), light emitting diodes (LEDs) 221, a analog-to-digital converter (ADC) 222, a radio frequency (RF) module 223, a 10 MHz clock oscillator 224 and operational amplifiers (op amps) 225; a Core Subsystem (CSS) 23 that includes a microcontroller 230; and a Power Supply Subsystem (PSS) 24 that includes a power source 240 (such as for example a replaceable battery) and other components that will be described below. The organization of the sensor electronics into subsystems facilitates the implementation of a novel power management technique, as will be explained in greater detail below.

The power source 240 provides all necessary power to the sensor array 210 and the other various electronic components of the sensor 1. In accordance with the present invention, the sensor 1 is configured such that it is capable of transmitting image data to the base station 2 from within a patient's mouth, and is further configured such that it is capable of transmitting to the base station image data representing multiple intraoral images without requiring that it be removed from the patient's mouth for power source or replacement. Preferably, the sensor 1 of the present invention is capable of capturing and transmitting images representing at least a full-mouth series of x-rays (typically 18 images) without requiring that the power source be replaced. To achieve this goal, power consumption of the sensor must be managed carefully and efficiently, to ensure that the limited-life power source on board the sensor 1 can provide power sufficient for the capturing and transmission of the requisite number of images.

All components are encapsulated in a hermetically sealed housing so as to be suitable for insertion into the human mouth. The sensor housing is opaque to visible light but radiolucent, i.e. pervious to x-rays. Preferably, the sensor is impervious to liquid penetration and resistant to mechanical damage as could occur if a patient bit on the device or if the device were dropped from standing height. The package is typically scant on available space since the sensor is preferably less than 6 mm thick. The various components must therefore be selected with an eye towards miniaturization. In a preferred embodiment, light emitting diodes (LEDs) 221 on the surface of the sensor packaging comprise a portion of DPSS 22, and are used to indicate status. The sensor body is manufactured from a material such as plastic, to allow carrier waves to be transmitted without interference.

The sensor array 210 preferably comprises a CMOS APS array, such as for example a CMOS APS array of the type described in U.S. Pat. No. 5,471,515 and U.S. Pat. No. 6,134,298 each of which is hereby incorporated by reference. Each pixel in the APS array includes one or more active transistors which perform gain or buffering functions.

The sensor array 210 may alternatively be a CCD, or some other type of solid state device capable of converting electromagnetic radiation into electrical signals. As used herein, the term radiation broadly encompasses all waves in the electromagnetic spectrum. In any case, the sensor array 210 may additionally comprise on top of the CMOS APS array, CCD or other solid state device, a scintillator layer which converts x-rays into visible light, and might further include disposed beneath the scintillator layer a fiber optic faceplate.

The remaining components of the sensor, including the remaining electronics of SSS 21 and the electronics of DPSS 22, CSS 23 and PSS 24, comprises all of the circuitry necessary to control the exposure and readout of an image, and to provide and manage the requisite electrical power. The specifics of such electronics will vary with the nature of the sensor array 210. In the preferred embodiment illustrated in FIG. 2, these electronics perform the functions of row driver circuitry, reset driven circuitry, column signal chain circuitry, column shift register circuitry and timing and control circuitry, among other things.

In one preferred embodiment of the present invention, SSS 21 includes a novel event detection module 211 that determines when radiation is incident on the sensor array 210 by monitoring the amount of electrical current drawn by the pixels of the sensor array. This novel technique is extremely advantageous, in that it provides a reliable mechanism for detecting the presence at radiation that consumes very little excess power, particularly in comparison with conventional techniques, such as those that use dedicated event-detection diodes. The technique of the present invention is based upon the observation that, in a CMOS imaging array or a CCD imaging array, the magnitude of current drawn by each pixel is itself sensitive to the presence of radiation on the pixel, such that the pixels draw much more current when exposed to radiation and much less when not exposed to radiation. In an APS array, this current is the photo-induced current which flows through each diode in the array. In a CCD, there is a similar phenomenon at the substrate bias or similar point. In either case, the amount of current drawn may be used as a means of event detection.

Figure 3:
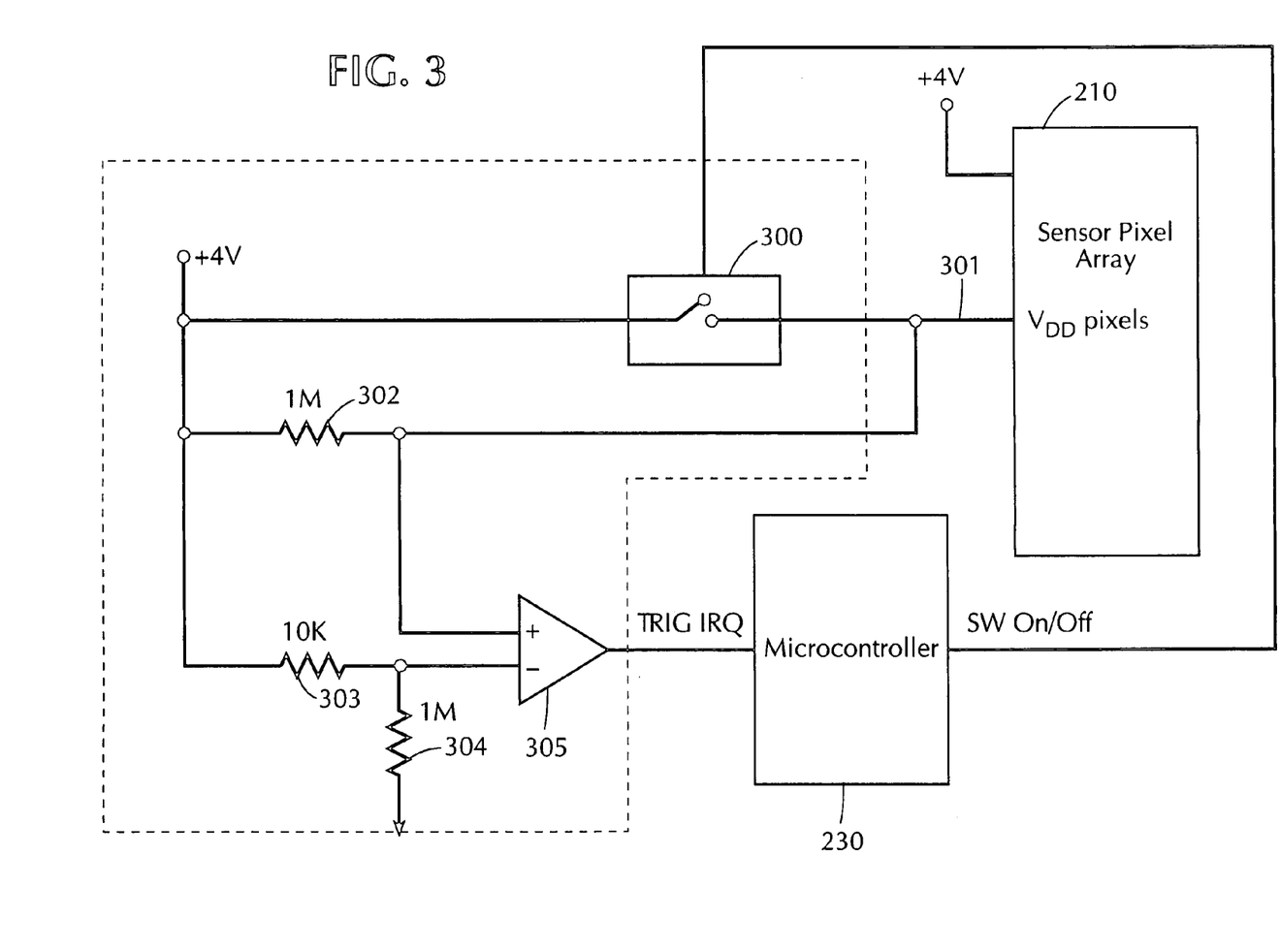
FIG. 3 is a schematic of a novel event detection circuit in accordance with one embodiment of the present invention.

The details of a suitable circuit for such an event detection module 211 are shown in FIG. 3. In FIG. 3, a bias voltage of +4V is connected to the input of a normally open switch 300, the output of which is connected to a supply line 301 that feeds the $V_{DD}$ input of each pixel. The +4V bias voltage is also connected to the supply line 301 through a large (1 MΩ) resistor 302 that is used as a current sensing device. When there is no radiation incident on the sensor array 210, the switch 300 is open and a very small current is drawn by the supply line 301 through the current sensing resistor 302. The presence of x-ray-radiation causes a step increase in the magnitude of the current drawn, which increase is sensed by resistor 302 to cause a corresponding step change in the voltage across it. This voltage change is detected by a comparator 305, which in turn generates a trigger interrupt request (TRIG IRQ) signal which it sends to the microcontroller 230. The TRIG IRQ signal indicates the presence of radiation, and causes the microcontroller 230 to generate a SW ON/OFF signal that closes the switch 300, and also to commence its routine to acquire the image from the sensor array 210. After the image acquisition routine is complete, the microcontroller re-opens the switch 300 and again enters the mode of waiting for another TRIG IRQ signal.

The magnitude of the step increase necessary to cause the comparator 305 to generate an TRIG IRQ signal is dependent upon the amounts of current drawn by the supply line 301 in the dark (non-irradiated) state and the irradiated state, the value of the current sensing resistor 302 and the values of resistors 303 and 304 which function as a voltage divider to generate a reference voltage. In the exemplary embodiment depicted in FIG. 3, the voltage divider is comprised of a 10 KΩ resistor 303 and a 1 MΩ resistor 304, the supply line 301 draws about 6 nA in the dark state and an TRIG IRQ signal is generated when there is a step increase to about 60 nA, representing a one order of magnitude increase in current.

During the image acquisition routine, analog data representing a captured image are read-out of the sensor array 210, conditioned by op-amps 225, converted to digital data by an analog-to-digital (ADC) 222 and provided to RF module 223 via the CPLD 220, all under the control of the microcontroller 230. The microcontroller 230 may be any suitable processor, such as for example a chip that comprises a reduced instruction set computer (RISC) and memory. An example of a suitable microcontroller is the MSP430F1121-A part manufactured and sold by Texas Instruments. The CPLD may be any appropriately programmed logic array of sufficient complexity, such as for example the Cool Runner part manufactured and sold by Xilinx.

The RF module 223, which may incorporate for example a Maxim MAX2750EUA voltage-controlled oscillator, transmits digital image data via an antenna and a wireless link. A high reliability RF link is essential since the data must be transmitted from the sensor from within a patient's mouth. Furthermore, because the amount of image data set is typically large, and transmission preferably should be nearly instantaneous, a high-speed link is required. The data are transmitted in digital form to ensure error-free transmission, although transmission of analog data is also possible.

In the CPLD 220, the native signal is divided into packets and encoded to Manchester format. In the RF module 223, a carrier is modulated with the resultant digital signal using frequency shift keying and transmitted at a frequency compliant with European and U.S. regulatory requirements. The effective transmission range is preferably at least ten feet, allowing clinicians freedom in where they choose to place the receiver. Preferably, RF module 223 transmits periodic carrier bursts to allow the host computer 3 to gauge the RF link status and insure that the sensor 1 is ready for use. The RF receiver 2a in base station 2 demodulates the modulated carrier to restore the original base band signal. Control logic may be implemented to facilitate operations such as the Manchester decoding, digital filtering, packet decoding and the suppression of unwanted signals. These steps help assure reliable communication between the base station and sensor as communication failures could result in unnecessary patient radiation exposure.

PSS 23 includes a power source 240, such as a replaceable battery 240 having sufficient service life which can provide enough power to capture at least a full-mouth series of x-ray images (typically eighteen exposures), and preferably several full-month series of images, when the novel techniques of the present invention are implemented. Suitable types of batteries include, but are not limited to, nickel-cadmium, nickel-metal-hydride, lithium manganese dioxide and lithium ion. Other options for the power source 240 are also possible, such as for example an ultra cap device.

In any case, the power source 240 must provide a significant amount of power to meet the needs of the circuitry and must be small enough to fit within the slim profile that is preferred clinically. The power source may, but need not be, rechargeable. Whether or not the power source is rechargeable, given the relatively large power requirements of a solid state image sensor, and the relatively limited amount of power available in a power source small enough to be integrated into an introral sensor, careful and creative power management must be employed to enable the sensor to take a full-mouth series without necessitating that the sensor be removed from the mouth for replacement, and/or, if applicable, recharging of the power source.

The above challenge was overcome principally by developing a novel sequence whereby the sensor functions in a variety of power states suited to its existing needs, conserving power when appropriate. Speaking generally, the sequence is as follows: the sensor is actuated prior to use, and remains in a low-power mode until triggered by the event detection circuitry. A high-power mode is utilized only briefly for acquiring and transmitting an image, after which the sensor returns to the low-power mode. This sequence prolongs the service life of the power source.

The novel power-saving technique of the present invention will now be described in greater detail. As is illustrated in FIG. 2, PSS 24 includes a low dropout (LDO) linear regulator 241 for providing an operating voltage (such as, for example, a 4.0V operating voltage) to SSS 21; an LDO regulator 242 for providing an operating voltage (such as, for example, a 3.0V operating voltage) to CSS 23; and a LDO regulator 243 for providing an operating voltage (such as, for example, a 3.0V operating voltage) to DPSS 22. As is illustrated, LDO 241 and LDO 243 are controlled by shut-down (SHDW) signals from the microcontroller 230, such that SSS 21 and DPSS 22 are provided with operating voltages only when those devices are enabled by their respective SHDW signals. LDO 242 is not controlled by an SHDW signal, and thus CSS 23 is always provided with an operating voltage. PSS 24 further includes a push-button switch 244 for providing a push-button switch interrupt (PBSW IRQ) request to CSS 23 (specifically, to microcontroller 230), thus functioning as a start-up button, which the practitioner may actuate to turn the sensor on or off.

Figure 4:
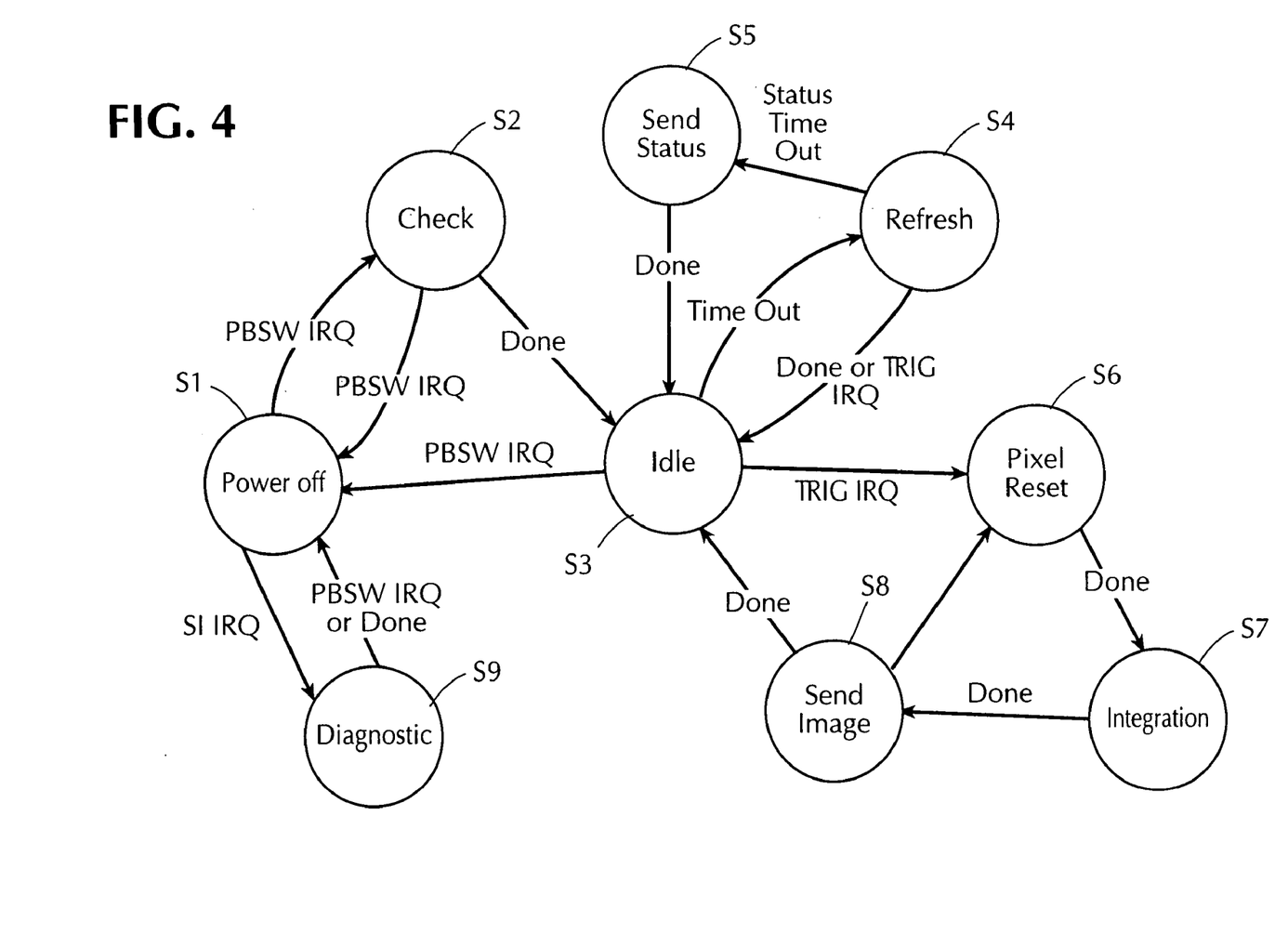
FIG. 4 is a state diagram illustrating various states of operation for the intraoral sensor of the present invention.

The manner in which the provision of power to the various components of the sensor is managed will now be described with reference to the state diagram of FIG. 4. In the power-off state (S1), an operating voltage is provided only to CSS 23; LDO 241 and LDO 243 are prevented from supplying operating voltages to SSS 21 and DPSS 22 (respectively) by the presence of SHDW signals from the microcontroller 230. In this state the microcontroller 230 is in the stand-by mode, and consumes very little power; all other components of course consume no power at all, since they are not provided with operating voltages. Thus, overall sensor power consumption in state S1 is extremely low. The duration of the power-off state S1 is indefinite: the sensor 1 remains in the power-off state S1 until the microcontroller 230 receivers either an interrupt PBSW IRQ or a serial interface interrupt request (SI IRQ), as will be explained below.

When the microcontroller 230 receives a PBSW IRQ (generated in response to the depression of push-button switch 245), the sensor 1 transitions to check state S2. In this state, the power source 240 is checked to ensure that there is enough power remaining sufficient for n images (e.g., 18 images for a full mouth series), and the RF link 4 is checked by transmitting identification (ID) data to the host computer 3. Accordingly, in the check state S2 the SHDW signal sent by the microcontroller 230 enables LDO 243 to provide an operating voltage to DPSS 22 to power the RF module 223 and other DPSS components that requires power (such as, for example, the LEDs 221, if they are to be used to indicate battery status). LDO 241 is disabled by a SHDW signal in state S2, so that no voltage is supplied to SSS 21. The duration of the check state S2 is predetermined, such as for example 10 ms. Before the expiration of that time period, the sensor can be forced out of the check state S2 and back to power-off state state S1 by a PBSW IRQ. Overall sensor power consumption in state S2 is moderate, but the sensor is in the state for a relatively short amount of time.

After the expiration of the predetermined (e.g. 10 ms) period, the sensor 1 transitions to the idle state S3. In this state, the SHDW signals produced by microcontroller 230 enable LDO 241 to provide an operating voltage to SSS 21, and disable LDO 243 so that no operating voltage is provided to DPSS 22. In this state, the sensor is simply waiting for the event detection circuit 211 to detect the presence of radiation and generate a TRIG IRQ signal. Accordingly, no clocks are provided to the sensor array 210, and the overall amount of power consumed by the sensor is very low. The sensor 1 may also be forced out of the idle state S3 into the power-off state S1 by a PBSW IRQ.

If no TRIG IRQ signal is generated within a predetermined period of time (such, as for example, 100 ms) following the transition of the sensor 1 into the idle state S3, a time-out occurs and the sensor transitions into the refresh state S4. In the refresh state S4, the sensor array 210 is refreshed to clear it of charge that has accumulated due to thermally generated currents (so-called dark current) during the idle time. To effect such refreshing, a global pixel reset (GPR) signal is sent by the microcontroller 230 to the sensor array 210. However, no clock signals are provided to the sensor array 210 by the CPLD 220. The SHDW signals enable both LDO 241 and LDO 243, to provide operating voltages to both SSS 21 and DPSS 22. However, the RF module 223 is kept off and uses no power, since no signals are transmitted from the sensor 1. Overall power consumption by the sensor 1 during S4 is moderate, but the sensor 1 remains in the refresh state S4 only for a very short, predetermined amount of time (such as for example 50 µs), after which it (typically) transitions back to the idle state S4. The sensor 1 may also be pulled from the refresh state S4 to the idle state S3 (and then to the pixel reset state S5 as described below) by the presence of an TRIG IRQ signal.

In a preferred embodiment, the sensor 1 may be designed such that once every n seconds (such as, for example, once every 5 seconds) it transitions from the refresh state S4 to a send status state S5, in which status data is transmitted from the sensor 1 to the base station 2. In the send status state S5, operating voltages are provided to each of SSS 21, DPSS 22 and CSS 23. No clocks are provided to the sensor array 210, and the RF module 223 is of course on, since it is transmitting data. The sensor 1 remains in the send status state S5 for a predetermined period of time, after which it transitions to the idle state S3. Power consumption in the send state status S5 is moderate.

When in the idle state S3, the sensor 1 will transition to the pixel reset state S5 upon receipt of a TRIG IRQ signal. Sensor activity is similar in the pixel reset state S5 as it is in the refresh state S4, in which operating voltages are sent to both the SSS 21 and DPSS 22. No clock signals are sent to the sensor array 210, the RF module is off and a GPR signal is sent to the sensor array 210. The sensor 1 remains in the pixel reset state S6 for a predetermined amount of time (such as, for example, 410 µs). Total power consumption during the pixel reset state S3 is moderate.

After the predetermined time (e.g. 410 µs), the sensor transitions 1 from the pixel reset state S6 to integration state S7, in which the sensor array accumulates charge in response to the incident radiation. In the integration state S7, no clocks are sent to the sensor array 210, the RF module 223 is off and the GPR signal is inactive. Total power consumption by the sensor S1 is low. The sensor S1 remains in the integration state S7 for a predetermined time, such as for example 700 ms, sufficient to allow the image to be acquired.

Following that predetermined amount of time, the sensor 1 transitions to the send image state S8, in which the accumulated data representing the acquired image is read out of the sensor array 210 and transmitted to the base station 2. During this state, the GPR signal is inactive, and clock signals are sent to the sensor array to read-out the image. The RF module is active, since the acquired data are transmitted to the base station 2. The duration of the send image state 8 is predetermined, such as for example 1200 ms. Power consumption during the send image state is high.

Following the send image state 8, the sensor 1 transition again to the pixel reset state S6, from there to the integration state S7 and from there to the send image state S8, with the operation and power consumption in each state being as described above. The salient difference between the first and second sequence and these states S6-S7-S8 is that during the second sequence there are no x-rays present, and the "image" that is acquired is a dark frame, representing the amount of charge accumulated due to dark cement. The dark frame is transmitted to the base station 2, and is ultimately subtracted from the image acquired in the first sequence S6-S7-S8 to produce the resultant image that is actually displayed. Following the second S6-S7-S8 sequences, the sensor 1 transitions back to the idle state S3.

By managing power in the manner discussed above, the dental practitioner is able to take multiple images using the sensor 1 of the present invention without needing to remove the sensor 1 from the patient's mouth for replacement or recharging of the power source 240. The present invention therefore allows the dentist to leave the sensor within or within the vicinity of the patient's mouth during the entirety of an examination, moving the sensor only as necessary to reposition it in order to take the next image, and not needing to remove it from the mouth to change or recharge the power source, or provide the acquired data to the base station.

When not in use, the sensor 1 is kept in the base station 2. In an embodiment in which the sensor utilizes a rechargeable battery, the base station 2 serves to electrically recharge it. Preferably, the base station 2 can accept sensors of varying sizes (such as, for example, size 0, size 1 and size 2 sensors), and may also be configured to accept multiple sensors.

The base station 2 interfaces with the sensor via serial interface 245, and can be constructed to configure and perform diagnostics on the sensor 1. Such diagnostics are initiated by the base station 2 sending to the sensor 1 a SI IRQ. More specifically, when the sensor 1 is in any of the power-off state S1, the receipt of a SI IRQ will cause the sensor to transition to the diagnostic state S9, in which a diagnostic program is run on the sensor and the resultant data generated by the diagnostics operation is provided to the base station 2. In this state operating voltages are provided to each of the SSS 21, DPSS 22 and CSS 23 and power consumption is high. However, power-conservation in the diagnostic state S9 is not an especially important consideration, since the sensor S1 may only be in that state when physically coupled to the base station, during which time the power source 240 may be recharged in the case where the power source 240 is a rechargeable battery.

Communication between the sensor 1, base station 2 and host computer 3 may be controlled by specialized firmware and software residing on the sensor 1 (more specifically, in the memory of the microcontroller 230), base station 2 and host computer 3. The data may be exported from the base station 2 using one or more of a multitude of commonly used ports, including the USB. In a preferred embodiment, the USB not only provides data output capability, but also supplies power to the base station. Power to the base station could of course be achieved through alternative means as will be apparent to those skilled in the art. USB management may be handled by the base station as well.

It is understood that the above description and drawings are illustrative of the present invention and detail contained therein are not to be construed as limitations thereon. Changes in components, procedure and structure may be made without departing from the scope of the present invention as defined in the following claims.

What we claim is:

1. An intraoral sensor, comprising:
   a radiation sensitive sensor array including a scintillator which converts x-rays into visible light radiation, and a plurality of pixels sensitive to visible light radiation to capture an image upon the presence of incident radiation;
   an event detection circuit including a current sensing device, said event detection circuit configured to generate a triggering signal indicating the presence of radiation incident on the sensor array based upon the amount of electrical current drawn by the sensor array; and
   a transmitter adapted to transmit via a wireless link signals representing an image captured by the sensor array.

2. The intraoral sensor according to claim 1, wherein the sensor array comprises a complementary metal oxide semiconductor active pixel sensor array.

3. The intraoral sensor according to claim 1, wherein the sensor array comprises a charge-coupled device.

4. The intraoral sensor according to claim 1, further comprising a power source comprising a battery.

5. The intraoral sensor according to claim 4, wherein the battery is rechargeable.

6. The intraoral sensor according to claim 1, wherein the transmitter is a radio frequency transmitter and wherein the wireless link is a wireless radio frequency link.

7. An intraoral sensor, comprising:
   means for converting x-rays into visible light radiation and capturing an image upon the presence of incident radiation;
   means for generating a triggering signal indicating the presence of radiation incident on said capturing means based upon the amount of electrical current drawn by said converting and capturing means; and
   means for transmitting via a wireless link signals representing an image captured by said converting and capturing means.

* * * * *